United States Patent [19]

Hirasawa et al.

[11] Patent Number: 5,710,039
[45] Date of Patent: Jan. 20, 1998

[54] PORPHYROMONAS GINGIVICANIS STRAIN ATCC 55562

[75] Inventors: Masatomo Hirasawa; Kazuko Takada, both of Chiba, Japan

[73] Assignee: Nihon University (Educational Foundationn), Tokyo, Japan

[21] Appl. No.: 520,790

[22] Filed: Aug. 30, 1995

[51] Int. Cl.$^6$ .................................................... C12N 1/20
[52] U.S. Cl. ................................................... 435/252.1
[58] Field of Search ........................................ 435/252.1

[56] References Cited

PUBLICATIONS

D. Love et al; "*Porphyromonas canoris*" sp Nov., an Asaccharolytic, Black–pigmented Species from the Gingival Sulcus of Dogs, International Journal of Systematic Bacteriology, Apr. 1994, pp. 204–208.

*Primary Examiner*—Irene Marx
*Attorney, Agent, or Firm*—Browdy and Neimark

[57] ABSTRACT

A novel species of microorganism of the genus Porphyromonas isolated from the gingival crevicular fluids of beagles, designated *Porphyromonas gingivicanis* and deposited with American Type Culture Collection (ATCC) under accession number 55562.

1 Claim, No Drawings

PORPHYROMONAS GINGIVICANIS STRAIN ATCC 55562

BACKGROUND OF THE INVENTION

1. Field of the Invention

The present invention relates to a novel species of microorganism belonging to the genus Porphyromonas and obtainable from the gingival crevicular fluids of beagles.

2. Description of the Background Art

Beagles are commonly used in periodontal disease research since periodontal disease can be experimentally induced in beagle gingival tissues (Hamp et al., *Arch. Oral. Biol.* 17:329–337, 1972; Hamp et al., *J. Periodontal Res.* 8:63–70, 1973; Schroeder et al., *Arch. Oral Biol.* 20:775–782, 1975). The microbial flora associated with this disease has also been extensively studied (Syed et al., *J. Periodontal Res.* 15:123–136, 1980; Syed et al., *J. Clin. Periodontal* 8:45–56, 1981).

Coykendall et al. (*J. Syst. Bacteriol.* 30:559–564, 1980) described the G+C contents of two Porphyromonas strains isolated from dog; the G+C content of one strain was 42 mol %, and the G+C content of the other was 48 mol %. Also, most of the catalase-positive dog strains of Porphyromonas described previously produced phenylacetic acid (Kaczmarek et al., *J. Clin. Microbiol.* 12:288–290, 1980). Laughon et al., *J. Clin. Microbiol.* 15:97–102, 1982, described beagle strains which may not have trypsin activity, α-glucosidase activity, or N-acetyl-β-glucosaminidase activity. Laliberté et al., *J. Appl. Bacteriol.* 55:247–252, 1983, who described 20 isolates obtained from 10 dogs, found that their strains were catalase positive, hemagglutinate erythrocytes, and have trypsin activity. However, in all of these cases, the descriptions of the biochemical parameters of the Porphyromonas strains isolated from nonprimate sources were incomplete.

SUMMARY OF THE INVENTION

The present invention provides a biologically pure culture of a novel species of Porphyromonas. This novel species, designated *Porphyromonas gingivicanis* is characterized by being black-pigmented, asaccharolytic, anaerobic, nonmotile, non-spore-forming, gram-negative, rod-shaped organisms. These organisms are obtainable from the gingival crevicular fluids of beagles. *P. gingivicanis* does not grow in the presence of 20% bile. They exhibit less than 5% DNA-DNA homology with the type strains of *Porphyromonas gingivalis* (strain ATCC 33277), *Porphyromonas endodontalis* (strain ATCC 35406), and *Porphyromonas asaccharolytica* (strain ATCC 25260), which were isolated from humans, or with the type strains of *Porphyromonas salivosa* (strain NCTC 11632) and *Porphyromonas circumdentaria* (strain NCTC 12469), which were isolated from cats. The major cellular fatty acid of *P. gingivicanis* is 13-methyltetradecanoic acid (iso-$C_{15:0}$ acid). Catalase, and glutamate and malate dehydrogenases are present and 6-phosphogluconate, glucose-6-phosphate dehydrogenases, and trypsin are absent. *P. gingivicanis* produces large amounts of acetic and isovaleric acids and minor amounts of isobutyric and succinic acids as end products of metabolism in GAM medium. *P. gingivicanis* also produces large amounts of butyric acid and small amounts of propionic acid. The G+C contents of the DNA of *P. gingivicanis* is 41 to 42 mol %. The type strain of *P. gingivicanis* is NUM 301 and was deposited as ATCC 55562.

DETAILED DESCRIPTION OF THE INVENTION

A number of asaccharolytic, black-pigmented, anaerobic bacteria, which have unique characteristics when compared with Porphyromonas species isolated from humans (Shah et al., *Int. J. Syst. Bacteriol.* 38:128–131, 1988), was isolated from the microbial flora in the gingival crevicular fluids from beagles. The present invention relates to a novel Porphyromonas species of microorganism, *Porphyromonas gingivicanis* (gin.gi.vi.ca'nis. L. fem. n. gingiva, the gums; L. gen. n. canis, of a dog; N.L. gen. n. gingivicanis, of the gums of a dog, because the organism was first isolated from gums of dogs) isolated from gingival crevicular fluids obtained from beagles. The isolation and initial characterization were carried out by the procedures described by Laliberté et al., supra, 1983, herein incorporated by reference. *P. gingivicanis* strains were maintained on GAM agar (Nissui, Tokyo, JAPAN) supplemented with 5% rabbit blood, 0.05% hemin, and 0.01% menadione in an atmosphere containing 80% $N_2$, 10% $CO_2$, and 10% $H_2$. The physiological, serological, and biochemical characteristics of this novel Porphyromonas species is presented below.

*P. gingivicanis* cells are obligately anaerobic, nonmotile, gram negative, and rod shaped (or coccoid) and do not form spores. On rabbit blood agar plates, the average size of cells is about 0.5 μm by 1.0 μm in diameter, and the cells occur singly. After 72 hours of incubation, surface colonies are about 0.8 to 1.5 mm in diameter, circular, entire, dome-shaped, opaque, and brown or black. Vitamin K and hemin are required for growth. Carbohydrate fermentation is not detected in a medium containing glucose, mannose, lactose, sucrose, cellobiose, trehalose, xylose, or arabinose. The G+C content of the DNA is in the range of about 41 to 42 mol %. The major fermentation products in GAM broth are acetic acid (average, 43.4 μmol/ml), butyric acid (average, 31.9 μmol/ml), and iso-valeric acid (average, 21.0 μmol/ml). Smaller quantities of isobutyric acid (average, 8.5 μmol/ml), succinic acid (average, 8.3 μmol/ml), and propionic acid (average, 1.4 μmol/ml) are produced. Iso-$C_{15:0}$ acid is the major cellular fatty acid. Malate and glutamate dehydrogenase activities are present, but 6-phosphogluconate dehydrogenase and glucose-6-phosphate dehydrogenase activities are not (see Table 1). Cells do not produce phenylacetic acid when grown in GAM medium and are catalase positive. *P. gingivicanis* cells neither agglutinate sheep erythrocytes nor exhibit trypsin or N-acetyl-β-glucosaminidase activity. The strains are susceptible to penicillin (0.5 U/disk), amoxicillin (2 μg/disk), sulbenicillin (5 μg/disk), and erythromycin (0.5 μg/disk) as determined with antibiotic disks (Eiken Chemical Co., Ltd., Tokyo, Japan).

*Porphyromonas gingivicanis* (NUM 301) was deposited on Apr. 11, 1994 with the American Type Culture Collection (ATCC), 12301, Parklawn Drive, Rockville, Md. 20852, as International Depository Authority in accordance with the Budapest Treaty on the International Recognition of the Deposit of Microorganisms for the Purposes of Patent Procedure under the accession number ATCC 55562 (originally designated *Porphyromonas nigreoricanis* at the time of deposit but renamed *Porphyromonas gingivicanis*).

Nonfermentative metabolism distinguished the novel Porphyromonas strains of the present invention from the genus Prevotella, and the absence of glucose-6-phosphate dehydrogenase and 6-phosphogluconate dehydrogenase and the presence of iso-$C_{15:0}$ as the major cellular fatty acid distinguish them from the *Bacteroides fragilis* group. Also, these novel isolates are biochemically and morphologically different from the other nonfermentative gram-negative anaerobic rods, including Bilophila, Desulfomonas, Dichelobacter, and Tissierella species. Bilophila, Desulfomonas, Dichelobacter, and Tissierella strains do not produce a black pigment, while the strains which we studied do produce a characteristic black pigment. These novel Porphyromonas strains do not grow in media containing 20% bile and are not susceptible to kanamycin, while Bilophila strains can grow under these culture conditions and are susceptible to kanamycin. Furthermore, the novel strains are indole positive and do not form colonies with spreading edges, while Dichelobacter strains do not produce indole and spreading of Dichelobacter colonies does occur.

In order to compare the novel Porphyromonas species with the previously described Porphyromonas species isolated from humans and cats, *Porphyromonas gingivalis* ATCC 33277$^T$ (T=type strain), *Porphyromonas endodontalis* ATCC 35406$^T$, and *Porphyromonas asaccharolytica* ATCC 25260$^T$ were obtained from the American Type Tissue Culture Collection and *Porphyromonas salivosa* NCTC 11632$^T$ and *Porphyromonas circumdentaria* NCTC 12469$^T$ were obtained from the National Collection of Type Cultures (NCTC).

EXAMPLE 1

Isolation of DNA

DNA was extracted from cells grown in 1 liter of GAM broth supplemented with menadione and hemin. The cells were harvested by centrifugation and then suspended in a 0.15M NaCl-0.01M EDTA-salt solution (pH 8.0). The cells were lysed by adding sodium dodecyl sulfate to a final concentration of 1%. The DNA was then extracted and purified by the method described by Marmur et al., *J. Mol. Biol.* 5:109–118, 1962.

Determination of the G+C contents of DNAs

The guanine-plus-cytosine (G+C) contents of the DNA preparations were determined by the High-Performance Liquid Chromatography (HPLC) method. Briefly, 10 µg of denatured DNA was hydrolyzed with P1 nuclease (50 µg/ml in 50 mM acetate buffer containing 0.1 mM $ZnCl_2$, pH 5.3; Yamasa Shoyu Co., Ltd., Chiba, JAPAN) for 2 hours at 50° C. Alkaline phosphatase (2.4×10$^{-2}$ U; Takara Shuzo Co., Ltd., Tokyo, JAPAN) was then added, and the mixture was incubated at 37° C. for 1 hour. The nucleosides were separated and quantified with a model 510 HPLC system (Waters, Millipore Co., Bedford, Mass.) and a Nova-Pak C18 column (Waters) by using an equal amount of a nucleoside mixture (Yamasa, Tokyo, JAPAN) as a standard. The nucleosides were eluted with a solvent containing 0.2M $NH_4H_2PO_4$ and acetonitrile (20:1, vol/vol).

The G+C contents of *P. gingivicanis* strains are quite different from the G+C contents of Tissierella and Desulfomonas strains. The strains isolated from beagles are therefore members of the genus Porphyromonas. These *P. gingivicanis* strains are distinctly different from the type strains of *P. gingivalis* (strain ATCC 33277), *P. endodontalis* (strain ATCC 35406), and *P. asaccharolytica* (strain ATCC 25260), which were isolated from humans. As shown in Table 1, the G+C contents of *P. gingivicanis* strains, including strains NUM 301$^T$, NUM 308, NUM 313, and NUM 325, which do not produce phenylacetic acid, are in the range of about 41 to 42 mol %. The G+C contents are similar to those of Porphyromonas strains isolated from cats.

TABLE 1

Characteristics of *Porphyromonas gingivicanis* strains isolated from gingival crevicular fluids of beagles and Porphyromonas type strains.

| Organism | | End Product | G + C content |
|---|---|---|---|
| Species | Strain | GAM broth* | (mol %) |
| *P. gingivicanis* | NUM 301$^T$ | A, p, B, ib, IV, s | 41–42 |
| | NUM 308 | A, p, B, ib, IV, s | 41–42 |
| | NUM 313 | A, p, B, ib, IV, s | 41–42 |
| | NUM 325 | A, p, B, ib, IV, s | 41–42 |
| *P. salivosa* | NCTC 11632$^T$ | A, B, IV, S, PA | 42–44 |
| *P. circumdentaria* | NCTC 12469$^T$ | A, B, IV, S, pa | 40–42 |
| *P. gingivalis* | ATCC 33277$^T$ | A, B, IV, S, PA | 48–49 |
| *P. endodontalis* | ATCC 35406$^T$ | a, b, ib, iv$^b$ | 49–50 |
| *P. asaccharolytica* | ATCC 25260$^T$ | A, P, B, IB, IV$^b$ | 53–54 |

*GAM broth was obtained from Nissui. Abbreviations: A and a, acetic acid; B and b, butyric acid; IB and ib, isobutyric acid; IV and iv, isovaleric acid; P and p, propionic acid; S and s, succinic acid; PA and pa, phenylacetic acid. Uppercase letters indicate major amounts (≧15 µmol/ml), and lowercase letters indicate minor amounts (<15 µmol/ml).

EXAMPLE 2

DNA was isolated according to Example 1 and assessed for level of DNA-DNA homology with other Porphyromonas type strains.

Assessment of DNA-DNA homology

Dot blot hybridization on nitrocellulose filters in which photobiotin-labeled DNA was used was performed by the method described by Ezaki et al., *J. Syst. Bacteriol.* 39:224–229, 1989. Briefly, 5 µl of photobiotin (Pierce, Rockford, Ill.) was mixed with an equal volume of a heat-denatured DNA solution (5 µg of DNA) in an Eppendorf tube. This mixture was then irradiated with a sun lamp (500 W) for 15 minutes. After irradiation, free photobiotin was removed by 2-butanol extraction. The biotinylated DNA was used for dot blot hybridization.

Table 2 shows the DNA-DNA homology results for representative strains isolated from beagles, human strains, and cat strains. Dot blot hybridization studies showed that *P. gingivicanis* exhibited levels of DNA-DNA homology of less than 5% with *P. gingivalis* ATCC 33277$^T$, *P. asaccharolytica* ATCC 25260$^T$, *P. endodontalis* ATCC 35406$^T$, *P. salivosa* NCTC 11632$^T$, and *P. circumdentaria* NCTC 12469$^T$.

TABLE 2

Levels of DNA-DNA homology for Porphyromonas type strains and strains isolated from beagles.

| Unlabeled DNA from: | | Level of homology with labeled from strain*: | | | | | |
|---|---|---|---|---|---|---|---|
| Species | Strain | NUM 301$^T$ | NUM 402$^T$ | NUM 501 | ATCC 33277$^T$ | ATCC 35406$^T$ | ATCC 25260$^T$ |
| P. gingivicanis | NUM 301$^T$ | A | E | E | E | E | E |
| | NUM 308 | A | E | E | E | E | E |
| | NUM 313 | A | E | E | E | E | E |
| | NUM 325 | A | E | E | E | E | E |
| P. salivosa | NCTC 11632$^T$ | E | E | E | E | E | E |
| P. circumdentaria | NCTC 12469$^T$ | E | E | E | E | E | E |
| P. gingivalis | ATCC 33277$^T$ | E | E | E | A | E | E |
| P. endodontalis | ATCC 35406$^T$ | E | E | E | E | A | E |
| P. asaccharolytica | ATCC 25260$^T$ | E | E | E | E | E | A |

*The following five DNA relatedness classes were defined: A, 75 to 100% homology; B, 50 to 75% homology; C, 25 to 50% homology; D, 5 to 25% homology; and E, <5% homology.

EXAMPLE 3

Biochemical Characterization

The methods used for general biochemical characterization, as well as the methods used to determine volatile fatty acid content and methylation of nonvolatile fatty acids, were the procedures described by Holdeman et al., *Anaerobe Laboratory Manual*, 4th ed., 1977, Virginia Polytechnic Institute and State University, Blacksburg, Va. and in the instructions for the Minitek anaerobic system (BBL Microbiology Systems, Cockeysville, Md.). The compounds used in the fermentation assays were glucose, sucrose, lactose, cellobiose, mannose, arabinose, trehalose, and xylose. Phenylacetic acid was detected in methylated samples as described by Assche (*J. Clin. Microbiol.* 8:614–615, 1978).

The fatty acids were analyzed by the method described by Moore et al (*Int. J. Syst. Bacteriol.* 36:271–280, 1987). A Shimadzu model GC-9A gas chromatograph equipped with a flame ionization detector and a model Chromatopac C-R3A integrator (Shimadzu Co., Tokyo, JAPAN) were used for detection. The organic phase was chromatographed on a 3% OV-225 column (0.3 by 300 cm; Shimadzu Co.) For fatty acid identification, a bacterial acid methyl ester CP mixture (Matreya, Inc., Pleasant Gap, Pa.) was used as the standard.

Production of catalase was tested by adding a few drops of 30% $H_2O_2$ to cell suspensions (Holdeman et al., *Anaerobe Laboratory Manual*, 4th ed., Virginia Polytechnic Institute and State University, Blacksburg, Va., 1977). Hemagglutination activity was determined with 48-hour cultures in microtiter plates containing sheep erythrocytes, and the results were scored on a scale from 0 to 3+ (Laliberté et al., supra, 1983).

Serological and Enzymatic Characterization

Formation of antigen-antibody complexes was determined by an agar gel diffusion method, using 1.2% agarose in 0:033-ionic strength Veronal buffer (pH 8.6).

The antisera against *P. gingivicanis* strains formed no detectable precipitates with sonic extracts of *P. gingivalis*, *P. asaccharolytica*, *P. endodontalis*, *P. salivosa*, and *P. circumdentaria* and reacted with antigens to the strains, respectively. Also, sera against the other members of the genus Porphyromonas yielded no lines of precipitations with strains. These results indicated that serological dissimilarity might differentiate Porphyromonas species obtained from humans and cats. Enzymatic activities were determined by using the API ZYM system (Analytab Products, Plainview, N.Y.) (Hofstad, *Med. Microbiol. Immunol.* 168:173–177, 1980; Laughon et al., supra, 1982).

Phenotypic characteristics that differentiate *P. gingivicanis* from other Porphyromonas species are shown in Table 3. The unique characteristics of *P. gingivicanis* include production of catalase, lack of phenylacetic acid production, absence of trypsin, and no hemagglutination of sheep erythrocytes.

TABLE 3

Major distinguishing characteristics of *P. gingivicanis*, and Porphyromonas type strains.

| Taxon | Catalase activity | Phenylacetic acid | Hemagglutination | Enzyme Activities | | |
|---|---|---|---|---|---|---|
| | | | | Trypsin | N-acetyl-β-gluco-saminidase | α-Fuco-sidase |
| P. gingivicanis | + | − | − | − | − | − |
| P. salivosa NCTC 11632$^T$ | + | + | − | + | + | − |
| P. circumdentaria NCTC 12469$^T$ | + | + | − | − | − | − |
| P. gingivalis | − | + | +++ | + | + | − |

TABLE 3-continued

Major distinguishing characteristics of *P. gingivicanis*, and Porphyromonas type strains.

| | | | | | Enzyme Activities | |
|---|---|---|---|---|---|---|
| Taxon | Catalase activity | Phenylacetic acid | Hemagglutination | Trypsin | N-acetyl-β-gluco-saminidase | α-Fuco-sidase |
| ATCC 33277[T] | | | | | | |
| *P. endodontalis* ATCC 35406[T] | − | − | − | − | − | − |
| *P. asaccharolytica* ATCC 25260[T] | − | − | − | − | − | + |

The novel species *P. gingivicanis* is frequently detected in the periodontal or subgingival pockets of beagles with periodontitis and its presence can be used as a diagnostic indicator for the onset of periodontal disease and development of the morbid state. Killed or attenuated whole cells of *P. gingivicanis* may be used in the vaccination (active immunization) of dogs to prevent periodontal disease. Pathogen specific antibodies produced by animals immunized against the surface antigens of *P. gingivicanis* may be used as a passive immunization for the prevention of periodontal disease.

Antibodies specific to the surface antigens of *P. gingivicanis* can be used to detect the presence of *P. gingivicanis* as a pathogen in the subgingival pockets of dogs. Both polyclonal and monoclonal antibodies can be used as diagnostic indicators in assays described below.

Polyclonal antibodies are heterogeneous populations of antibody molecules derived from the sera of animals immunized with an antigen whereas monoclonal antibodies (mAbs) are a substantially homogeneous population of antibodies to specific antigens. In order to obtain a source of polyclonal or monoclonal antibodies specific to the surface antigens of *P. gingivicanis*, animals such as mice, rats, hamsters, and rabbits can be immunized with whole cells or purified surface antigens according to methods known to those skilled in the art. See, for example, Hartlow et al., *Antibodies: A Laboratory Manual*, Chapter 5, Cold Spring Harbor Laboratory press, Cold Spring Harbor, N.Y. (1988).

Monoclonal antibodies may be obtained by methods known to those skilled in the art. See, for example Kohler et al., *Nature* 256:495–497 (1975) and U.S. Pat. No. 4,376,110; de St. Groth, et al., *J. Immunol. Methods*, 35:1–21 (1980), Hartlow et al., *Antibodies: A Laboratory Manual*, Chapter 5, Cold Spring Harbor Laboratory press, Cold Spring Harbor, N.Y. (1988); *Monoclonal Antibodies and Hybridomas: A New Dimension in Biological Analyses*, Plenum Press, New York, N.Y. (1980); Campbell, "Monoclonal Antibody Technology," In: *Laboratory Techniques in Biochemistry and Molecular Biology*, Volume 13, Burdon et al. (eds.), Elsevier, Amsterdam (1984); and *Current Protocols in Immunology*, Volume 1, Chapter 2, Coligan et al. (eds.), Greene Publ. Assoc. and John Wiley & Sons, Inc. (1992–1995), which are hereby incorporated by reference. Such antibodies may be of any immunoglobulin class including IgG, IgM, IgE, IgA and any subclass thereof. The hybridoma producing the mAbs of this invention may be cultivated in vitro or in vivo. Briefly, for in vivo production, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Polyclonal antibodies may also be obtained by well-known methods and can be selectively purified for those antibodies specific for *P. gingivicanis* surface antigens by using techniques such as immunoaffinity columns. Hartlow et al., supra, and *Current Protocols in Immunology*, supra, provide examples of well-known methods for the purification of monoclonal and polyclonal antibodies.

A diagnostic assay for the presence of *P. gingivicanis* typically would comprise incubating a biological sample taken from a dog in the presence of a detectably labeled antibody capable of identifying the surface antigen(s) of *P. gingivicanis*, and detecting the binding molecule which is bound in a sample.

A biological sample may be treated with nitrocellulose, or other solid support which is capable of immobilizing cells, cell particles or soluble proteins. The support may then be washed with suitable buffers followed by treatment with the detectably labeled antibody. The solid phase support may then be washed with the buffer a second time to remove unbound antibody. The amount of bound label on said solid support may then be detected by conventional means.

A solid phase support is intended to mean any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

One of the ways in which the *P. gingivicanis* surface antigen-specific antibody can be detectably labeled is by linking the same to an enzyme and used in an enzyme immunoassay (EIA), or enzyme-linked immunosorbent assay (ELISA). This enzyme, in turn, when later exposed to its substrate, will react with the substrate in such a manner as to produce a chemical moiety which can be detected, for example, by spectrophotometric, fluorometric or by visual means. Enzymes which can be used to detectably label the *P. gingivicanis* surface antigen-specific antibody include malate dehydrogenase, staphylococcal nuclease, delta-V-steroid isomerase, yeast alcohol dehydrogenase, alphaglycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

Detection may be accomplished using any of a variety of immunoassays. For example, by radioactively labeling the *P. gingivicanis* surface antigen-specific antibodies or antibody fragments, it is possible to detect the presence of *P. gingivicanis* surface antigens through the use of a radioimmunoassay (RIA). A good description of RIA may be found in *Laboratory Techniques and Biochemistry in Molecular Biology*, by Work, T. S., et al., North Holland Publishing Company, N.Y., (1978) with particular reference to the chapter entitled "An Introduction to Radioimmune Assay and Related Techniques" by Chard, T., incorporated herein by reference.

The radioactive isotope can be detected by such means as the use of a gamma counter or a scintillation counter or by audioradiography. Isotopes which are particularly useful for the purpose of the present invention are: $^3H$, $^{125}I$, $^{131}I$, $^{35}S$, $^{14}C$, and preferably $^{125}I$.

It is also possible to label the *P. gingivicanis* surface antigen-specific antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The *P. gingivicanis* surface antigen-specific antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the *P. gingivicanis* surface antigen-specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the *P. gingivicanis* surface antigen-specific antibody may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

All references cited in this specification are hereby incorporated by reference.

What is claimed is:

1. A biologically pure culture of *Porphyromonas gingivicanis* ATCC 55562.

* * * * *